United States Patent
Lee et al.

(10) Patent No.: US 12,372,495 B2
(45) Date of Patent: Jul. 29, 2025

(54) INTERFACE CIRCUIT AND DIFFERENTIAL INTERFACE CIRCUIT WITH INTEGRATED COMPLEMENTARY SENSORS

(71) Applicant: Seoul National University R&DB FOUNDATION, Seoul (KR)

(72) Inventors: Jong-Ho Lee, Seoul (KR); Yu-Jeong Jeong, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 737 days.

(21) Appl. No.: 17/540,916

(22) Filed: Dec. 2, 2021

(65) Prior Publication Data
US 2023/0098591 A1    Mar. 30, 2023

(30) Foreign Application Priority Data
Sep. 28, 2021    (KR) .......... 10-2021-0128292

(51) Int. Cl.
*G01N 27/414* (2006.01)
*G01N 33/00* (2006.01)
(Continued)

(52) U.S. Cl.
CPC ..... *G01N 27/4141* (2013.01); *G01N 33/0031* (2013.01); *H10D 30/68* (2025.01)

(58) Field of Classification Search
CPC .......... G01N 27/4141; G01N 27/12
See application file for complete search history.

(56) References Cited

U.S. PATENT DOCUMENTS

| | | | |
|---|---|---|---|
| 2007/0216383 A1* | 9/2007 | Al-Shyoukh | G05F 1/468 323/280 |
| 2013/0273664 A1* | 10/2013 | Toumazou | G01N 27/4148 257/253 |

(Continued)

FOREIGN PATENT DOCUMENTS

| | | | | |
|---|---|---|---|---|
| CN | 104062327 B | * | 6/2016 | |
| CN | 105758898 A | * | 7/2016 | ............. G01N 27/12 |

(Continued)

*Primary Examiner* — Peter Bradford
(74) *Attorney, Agent, or Firm* — CANTOR COLBURN LLP (57) ABSTRACT

Provided is a complementary sensors-integrated interface circuit and a differential circuit using the same. The complementary sensors-integrated interface circuit includes: a first sensor having a sensing characteristic for a detection target material; and a second sensor having a sensing characteristic complementary to that of the first sensor for the detection target material, wherein the first sensor is composed of an FET-type sensor, the second sensor is composed of an FET-type sensor or a resistor-type sensor, and the first sensor and the second sensor are connected in series. The interface circuit having the above-described configuration increases the change in output voltage, thereby improving the sensing sensitivity. The complementary sensors-integrated interface circuit is characterized in that it serves as an amplification circuit. In addition, a complementary sensors-integrated differential interface circuit uses the aforementioned complementary sensors-integrated interface circuit, thereby serving as a differential amplifier circuit, reducing noise and improving sensitivity.

17 Claims, 10 Drawing Sheets

(51) Int. Cl.
    *H01L 29/788*     (2006.01)
    *H10D 30/68*     (2025.01)

(56) References Cited

U.S. PATENT DOCUMENTS

2017/0350853 A1\* 12/2017 Lee ..................... G01N 27/002
2022/0069712 A1\* 3/2022 Mondal ............... H02M 1/0009

FOREIGN PATENT DOCUMENTS

| CN | 118524917 | A | * | 8/2024 | ............ | B29C 45/00 |
|----|-----------|---|---|--------|--------------|------------|
| EP | 3444597 | A1 | * | 2/2019 | ............ | G01N 27/12 |
| JP | 56137146 | A | * | 10/1981 | | |
| JP | 2013250087 | A | * | 12/2013 | | |
| JP | 2014190698 | A | * | 10/2014 | | |
| JP | 2014190699 | A | | 10/2014 | | |
| KR | 20030088355 | A | | 11/2003 | | |
| KR | 20160037149 | | | 4/2016 | | |
| KR | 20170137641 | | | 12/2017 | | |
| KR | 20170137641 | A | | 12/2017 | | |
| KR | 20200080481 | A | * | 7/2020 | | |

\* cited by examiner

INTERFACE CIRCUIT AND DIFFERENTIAL INTERFACE CIRCUIT WITH INTEGRATED COMPLEMENTARY SENSORS

TECHNICAL FIELD

The present invention relates to a sensor interface circuit, and more specifically to a complementary sensors-integrated interface circuit that increases the output voltage for a detection signal and improves the detection sensitivity by combining two or more sensors having complementary detection characteristics with respect to a detection target material and a complementary sensors-integrated differential interface circuit using the above-described interface circuit.

BACKGROUND ART

Recently, as indoor and outdoor air pollution is getting worse, there is a demand and interest in chemical sensors or biosensors that can monitor harmful substances in the air through gas detection or diagnose diseases by detecting gases contained in human exhalation. In particular, as we enter the era of the Internet of Things (IoT), various types of sensors are needed to establish an Internet of Things (IoT) environment that can periodically monitor information on the surrounding environment, and also sensors that operate stably and with low power are required. Accordingly, research and development on these sensors are increasing. According to these needs and demands, the global gas sensor market is rapidly growing, and optical, electrical, chemical, and semiconductor-based gas sensors are being researched and developed in various ways.

Among the above-mentioned sensors, in the case of a semiconductor-based sensor, a metal oxide is used as a sensing material, and various sensor platforms such as resistance and FET type exist. Compared to optical and electrochemical sensors, semiconductor-based sensors have the advantages of smaller size and lower power consumption, as well as the ability to manufacture many sensors at a low process price. Among semiconductor-based sensors, the resistor-type sensor has a very simple structure in which a metal oxide semiconductor is deposited on a metal electrode, so the process is simple and a large amount of sensors can be produced at a low price, while the sensing material is used as a path for the output signal. Therefore, the noise of the sensor signal is very large and there is a limit in reliability and durability. On the other hand, the FET-type sensor can reduce the noise level because the sensing material and the FET channel are separated. Therefore, reliability and durability can also be improved.

Due to these characteristics, the FET-type sensor is being discussed as a strong candidate that can be utilized in the construction of an Internet of Things environment because it is stable, operates with low power, has low noise, and is compatible with a CMOS process.

Meanwhile, in addition to a sensor that operates stably to build an Internet of Things environment, a processor capable of reading and processing a signal output from the sensor is required. Most sensors currently being developed output sensing signals in the form of currents according to a reaction with a detection target. However, since the voltage output is less affected by noise than the current output, a processor that processes a detection signal of a sensor generally prefers the voltage output for stable signal processing.

On the other hand, most conventional chemical sensor or biosensor technologies use a resistor-type sensor, and conventional circuits using the resistor-type sensor configure an interface circuit using a fixed resistor as a load. Accordingly, the interface circuits using the resistor-type sensor configure a Wheatstone bridge circuit or a voltage division circuit using a fixed resistor that does not respond to a detection target to amplify the voltage output. However, this method has a problem in that in order to maximize the sensitivity of the circuit, the size of the load resistance must be used differently according to the response degree of the resistor-type sensor.

In addition, in case of the TFT-type sensor, an interface amplifier circuit is configured by using a fixed resistor or a TFT element that responds to the detection target as a load. However, this type has a problem in that the sensitivity of the circuit cannot be increased because the direction of current change is the same when the TFT-type sensor and the load respond to the detection target.

Accordingly, the present invention intends to propose a method capable of increasing the sensitivity of the sensor circuit.

SUMMARY

In order to solve the above problems, the present invention aims to provide a complementary sensors-integrated interface circuit that is configured to amplify a detection signal using sensors having complementary sensing characteristics to improve the sensitivity of the circuit.

According to a first aspect of the present invention for achieving the above-described technical problem, there is provided a complementary sensors-integrated interface circuit which comprises: a first sensor having a first sensing characteristic for a detection target material; and a second sensor having a second sensing characteristic for the detection target material, which the first and the second sensing characteristics to the detection target material are complementary to each other, wherein the first sensor is composed of an FET-type sensor and the second sensor is composed of an FET-type sensor or a resistor-type sensor and the first sensor and the second sensor are connected in series.

In the complementary sensors-integrated interface circuit according to the first aspect of the present invention, preferably the first sensor is composed of an FET-type sensor having a p-type or n-type channel, and the second sensor is composed of a resistor-type sensor or an FET-type sensor with a channel of a type opposite to that of the first sensor.

The complementary sensors-integrated interface circuit according to the first aspect of the present invention is characterized in that it has an amplification function, and as an example of this amplifier, it serves as an amplification circuit that converts a change in current according to a detection target material into a voltage output.

According to a second aspect of the present invention, there is provided a complementary sensors-integrated differential interface circuit that serves as a differential amplifier circuit constructed using the complementary sensors-integrated interface circuit.

The complementary sensors-integrated differential interface circuit according to the second aspect of the present invention comprises first and second circuit units arranged in parallel with each other, and a constant current supply element connected in series to one end of the first and second circuit units, wherein the first and second circuit units are provided with first and second sensors having sensing characteristics for a detection target material connected in series, the first sensor is composed of an FET-type sensor, the second sensor is composed of a FET-type sensor or a resistor-type sensor, and a first output and a second output are provided between the first and second sensors connected in series in the first and second circuit units, and the first and second sensors of the first and second circuit units are configured so that signals are complementary to each other.

Preferably, the complementary sensors-integrated differential interface circuit according to the second aspect of the present invention comprises first and second circuit units arranged in parallel with each other, and a constant current supply element connected in series to one end of the first and second circuit units, wherein the first and second circuit units are provided with first and second sensors each having a sensing characteristic for a detection target material connected in series, and the first sensor is composed of an FET-type sensor and the second sensor is composed of an FET-type sensor, wherein the second sensors in the first and second circuit units are connected to each other to constitute a current mirror circuit. A first output is provided between the first and second sensors of the first circuit unit and a second output is provided between the first and second sensors of the second circuit, and the first and second sensors of the first and second circuit units are configured so that signals of the first and second outputs are complementary to each other.

The complementary sensors-integrated interface circuit according to the present invention constitutes a circuit by combining sensors having complementary sensing characteristics with respect to a detection target material, thereby increasing the change in output voltage compared to a conventional circuit, so that the sensitivity of the circuit to the detection target material can be improved.

In addition, since the complementary sensors-integrated interface circuit according to the present invention can fabricate sensors having complementary sensing characteristics, such as a resistor-type sensor and an FET-type sensor having n-channel and p-channel, in a single process, the circuit can be configured in various combinations and the fabrication process can be minimized.

On the other hand, the sensor for configuring the circuit according to the present invention can be used in various ways, such as a chemical sensor, a biosensor, etc. as well as a gas sensor.

DETAILED DESCRIPTION

Hereinafter, with reference to the accompanying drawings, the configuration and operation of the complementary sensors-integrated interface circuit according to preferred embodiments of the present invention will be described in detail.

Example 1

Hereinafter, the configuration and operation of the complementary sensors-integrated interface circuit according to Example 1 of the present invention will be described in detail. In this patent specification, the term "having complementary sensing characteristics" means that when two sensors respond to the same detection target, the direction of change of current due to the response is opposite to each other. Therefore, in order to construct a combination of sensors having complementary sensing characteristics, a sensor operating with a different mechanism may be used, a sensor operating with the same mechanism may be used with a different type of sensing material, or a sensor with a different channel doping type may be used. In addition, in this patent specification, the term "detection target material" refers to a material that reacts with a sensing material of a sensor to cause a change in a sensor signal, and includes gas molecules or ions.

A complementary sensors-integrated interface circuit according to Example 1 of the present invention comprises: a first sensor having a first sensing characteristic for a detection target material; and a second sensor having a second sensing characteristic for the detection target material, which the first characteristic and the second characteristic for the detection target material are complementary to each other, wherein the first sensor is composed of an FET-type sensor and the second sensor is composed of an FET-type sensor or a resistor-type sensor and the first sensor and the second sensor are connected in series. Herein, the first sensor may be composed of an FET-type sensor having a p-type or n-type channel, and the second sensor may be composed of a resistor-type sensor or an FET-type sensor having a channel of the opposite type to that of the first sensor. In addition, the complementary sensors-integrated interface circuit according to Example 1 of the present invention is characterized in that it serves as an amplifying circuit.

Preferably, the complementary sensors-integrated interface circuit according to the present Example obtains a current or voltage signal at a point where the first sensor and the second sensor are connected and provides the obtained current or voltage signal as an output signal. In addition, the output signal of the complementary sensors-integrated interface circuit may be used in connection with a neuron circuit having a function of converting a pulse train or a pulse width.

Figure 1:
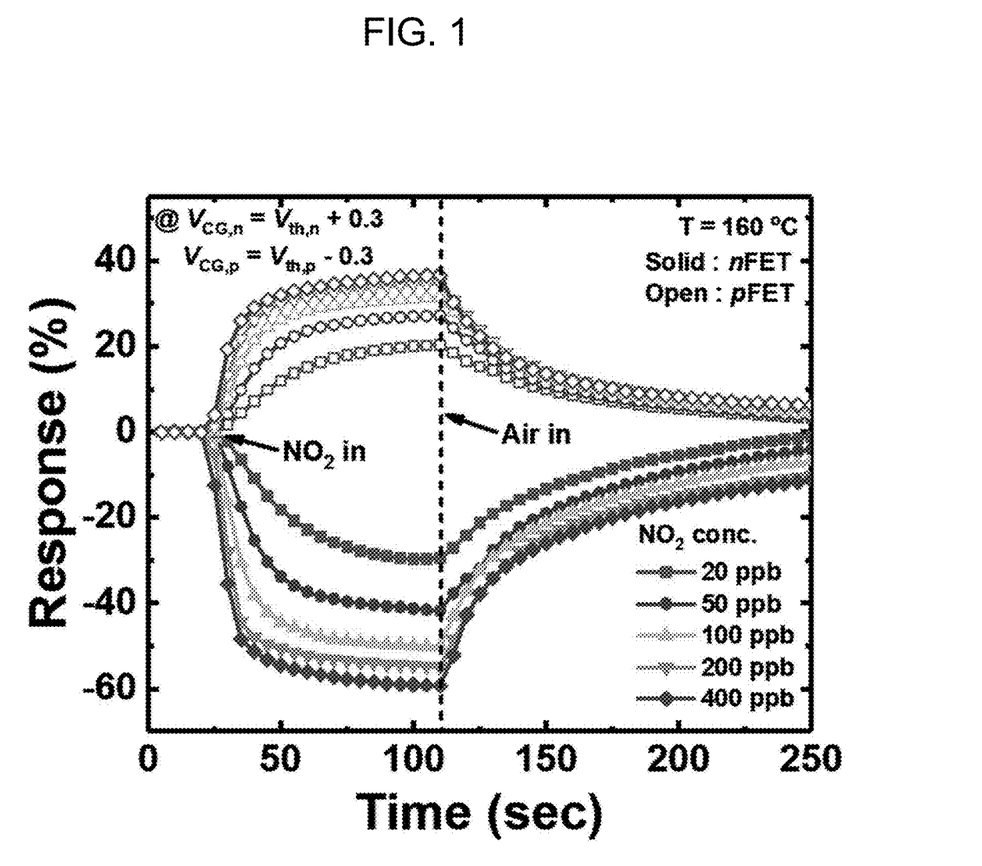
FIG. 1 is a graph showing gas response characteristics for a FET-type sensor having an n-type channel and a FET-type sensor having a p-type channel.
Figure 2:
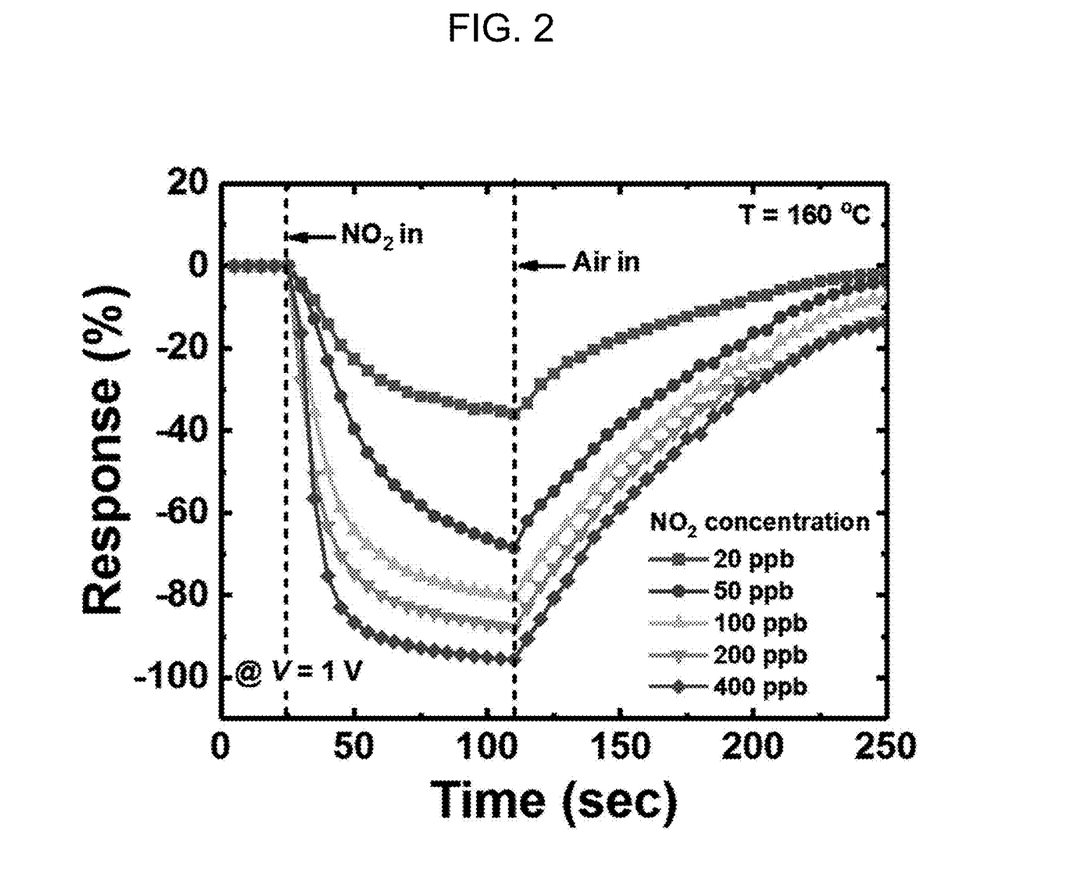
FIG. 2 is a graph of gas response characteristics for a resistor-type sensor.

FIG. 1 is a graph showing gas response characteristics for an FET-type sensor having an n-type channel and a FET-type sensor having a p-type channel. Referring to FIG. 1, it can be seen that a FET-type sensor having an n-type channel (a nFET-type sensor) and a FET-type sensor having a p-type channel (a pFET-type sensor) have complementary response characteristics. Meanwhile, FIG. 2 is a graph showing gas response characteristics for a resistor-type sensor. Referring to FIG. 2, it can be seen that the resistor-type sensor has response characteristics complementary to that of the pFET-type sensor of FIG. 1.

Figure 3:
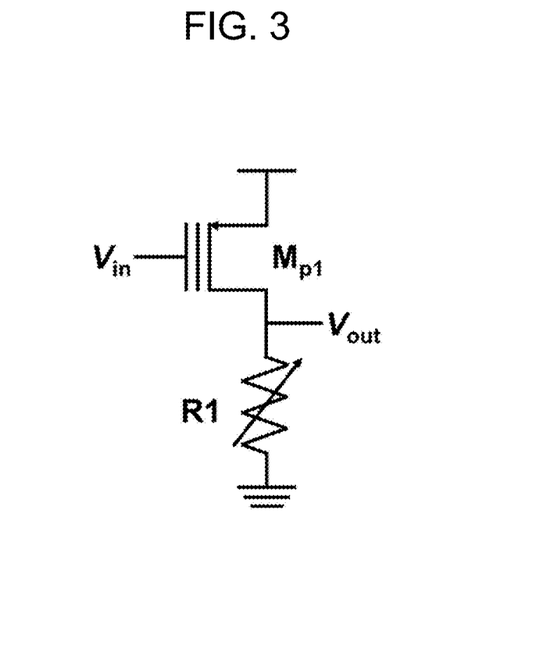
FIG. 3 is a circuit diagram of the first embodiment in the complementary sensors-integrated interface circuit according to Example 1 of the present invention.

FIG. 3 is a circuit diagram of the first embodiment in the complementary sensors-integrated interface circuit according to Example 1 of the present invention. Referring to FIG. 3, in the complementary sensors-integrated interface circuit according to the present embodiment, the first sensor ($M_{p1}$) composed of a pFET-type sensor, and the second sensor (R1) is composed of a resistor-type sensor.

When it reacts with the detection target material having the characteristics of an oxidizing gas, the current of the pFET-type sensor ($M_{p1}$) with the n-type sensing material serving as the first sensor increases, while the resistance of the resistor-type sensor (R1) with the n-type sensing material serving as the second sensor increases. At this time, as the current of the pFET-type sensor ($M_{p1}$) flows to the resistor-type sensor (R1), the output voltage ($V_{out}$) increases. As a result, in the circuit according to the present embodiment, the change in the output voltage of the circuit increases due to the effect that the change in the current of the pFET-type sensor serving as the first sensor and the change in the resistance of the resistance-type sensor serving as the second sensor are added. As described above, the sensitivity of the circuit may be improved as the change in the output voltage increases due to the sensing response to the gas or the like.

Figure 4:
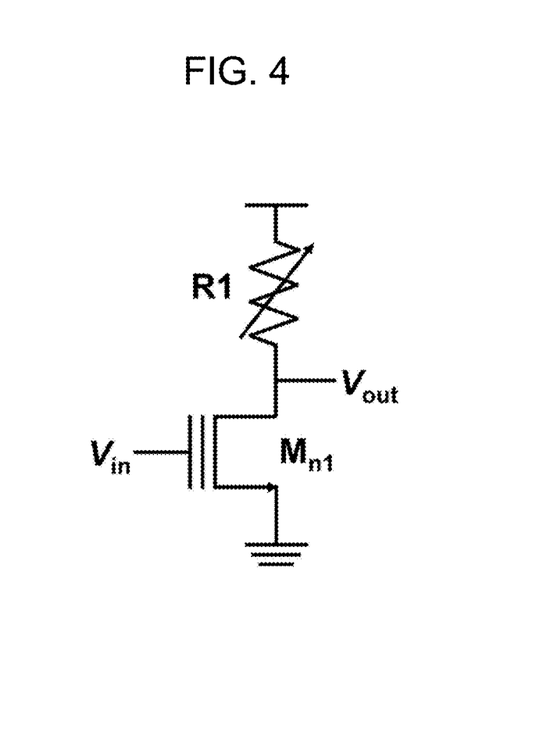
FIG. 4 is a circuit diagram of a second embodiment in the complementary sensors-integrated interface circuit according to Example 1 of the present invention.

FIG. 4 is a circuit diagram of a second embodiment in the complementary sensors-integrated interface circuit according to Example 1 of the present invention. Referring to FIG. 4, in the complementary sensors-integrated interface circuit according to the present embodiment, the first sensor ($M_{n1}$) is composed of an nFET-type sensor, and the second sensor is composed of a resistor-type sensor.

When it reacts with a detection target material having characteristics of an oxidizing gas, the current of the nFET-type sensor ($M_{n1}$) with a p-type sensing material serving as the first sensor decreases, while the resistance of the resistor-type sensor (R1) with the p-type sensing material serving as the second sensor decreases. At this time, as the current of the nFET-type sensor ($M_{n1}$) flows to the resistor-type sensor (R1), the output voltage ($V_{out}$) is decreased. As a result, in the circuit according to the present embodiment, the change in the output voltage of the circuit increases due to the effect that the change in the current of the nFET-type sensor serving as the first sensor and the change in the resistance of the resistance-type sensor serving as the second sensor are added. As described above, as the change in the output voltage increases due to the sensing response to gas or the like, it operates in a manner similar to that of the first embodiment described above, and as a result, the sensitivity of the circuit can be improved.

Figure 5:
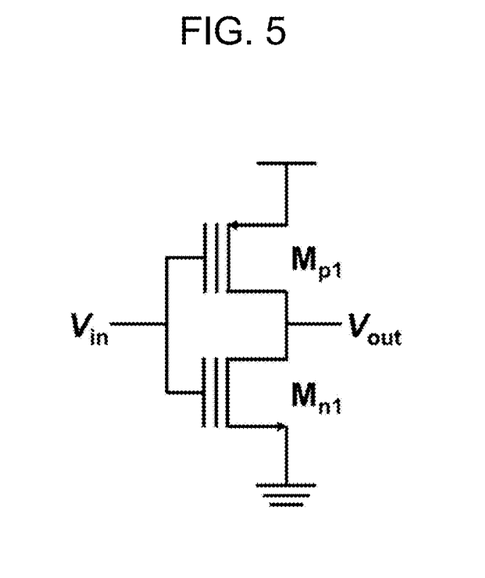
FIG. 5 is a circuit diagram of a third embodiment in the complementary sensors-integrated interface circuit according to Example 1 of the present invention.

FIG. 5 is a circuit diagram of a third embodiment in the complementary sensors-integrated interface circuit according to Example 1 of the present invention. Referring to FIG. 5, in the complementary sensors-integrated interface circuit according to the present embodiment, the first sensor ($M_{p1}$) is composed of a pFET-type sensor, and the second sensor ($M_{n1}$) is composed of an nFET-type sensor. The circuit according to the third embodiment shown in FIG. 5 is similar to that of the first embodiment described above, as the first sensor and the second sensor have complementary sensing characteristics with respect to the detection target material. In this way, the sensitivity of the circuit can be improved as a result.

Figure 6:
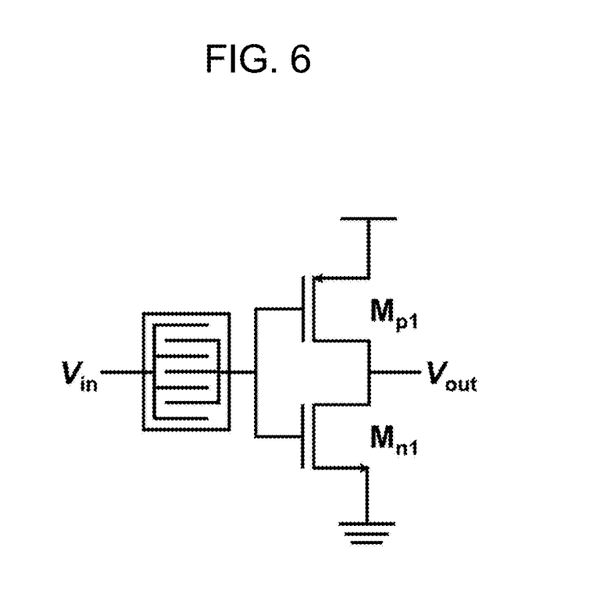
FIG. 6 is a circuit diagram of a fourth embodiment in the complementary sensors-integrated interface circuit according to Example 1 of the present invention.

FIG. 6 is a circuit diagram of a fourth embodiment in the complementary sensors-integrated interface circuit according to Example 1 of the present invention. Referring to FIG. 6, in the complementary sensors-integrated interface circuit according to this embodiment, it has the same structure as that of the third embodiment of FIG. 5, but the first sensor and the second sensor share a sensing material layer with each other and the same input power is applied.

Figure 7:
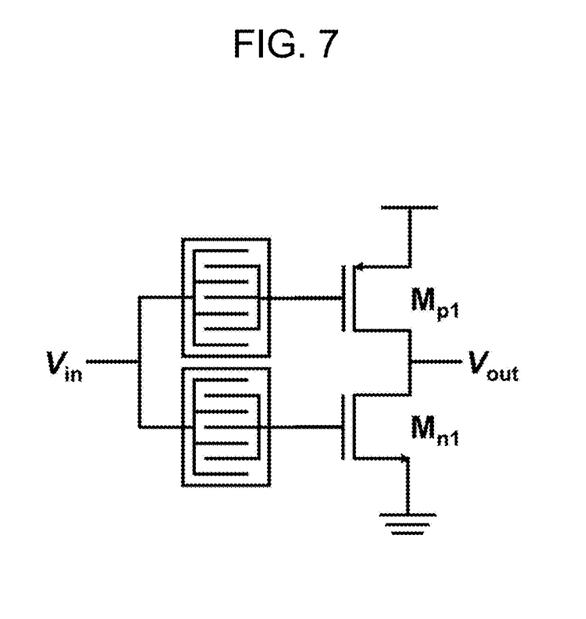
FIG. 7 is a circuit diagram of a fifth embodiment in the complementary sensors-integrated interface circuit according to Example 1 of the present invention.

FIG. 7 is a circuit diagram of a fifth embodiment in the complementary sensors-integrated interface circuit according to Example 1 of the present invention. Referring to FIG. 7, in the complementary sensors-integrated interface circuit according to the present embodiment, the first sensor and the second sensor each have a separate sensing material layer, while the same input power is applied, so that the gate electrode shares with each other.

Figure 8:
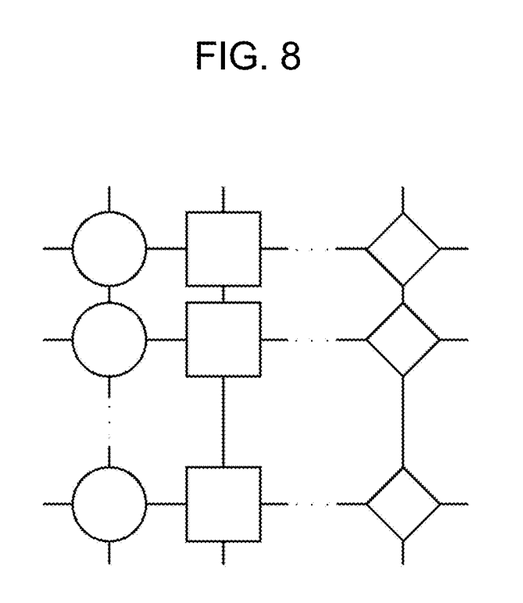
FIG. 8 schematically illustrates a complementary sensors-integrated interface circuit array composed of complementary sensors-integrated interface circuits according to Example 1 of the present invention.

FIG. 8 schematically illustrates a complementary sensors-integrated interface circuit array composed of complementary sensors-integrated interface circuits according to Example 1 of the present invention. Referring to FIG. 8, the complementary sensors-integrated interface circuits according to Example 1 of the present invention described above may be connected to each other to form a complementary sensors-integrated interface circuit array. In this case, each component constituting the array may be configured by a combination of various embodiments of Example 1 described above.

Example 2

Hereinafter, the configuration and operation of a complementary sensors-integrated differential interface circuit according to Example 2 of the present invention will be described in detail.

The complementary sensors-integrated differential interface circuit according to Example 2 of the present invention is configured based on the complementary sensors-integrated interface circuit according to Example 1 described above, and functions as a differential amplifier circuit.

The complementary sensors-integrated differential interface circuit according to the first embodiment of Example 2 of the present invention comprises: first and second circuit units arranged in parallel with each other, and a constant current supply element connected in series to one end of the first and second circuit units. In the complementary sensors-integrated differential interface circuit according to Example 2 of the present invention, the first and second circuit units are configured by serially connecting first and second sensors having sensing characteristics for a detection target material, respectively, and the constant current supply element provides constant current power to the first and second circuit units. The first and second circuit units configured based on the complementary sensors-integrated interface circuit comprises first and second sensors connected in series to each other, respectively. In the first and second circuit units, the first sensors are composed of an FET-type sensor, and the second sensors are composed of an FET-type sensor or a resistor-type sensor. A first output and a second output are respectively provided between the first and second sensors connected in series in the first and second circuit units, and the first and second sensors in the first and second circuit units are configured so that signals of the first and second outputs are complementary to each other.

Figure 9:
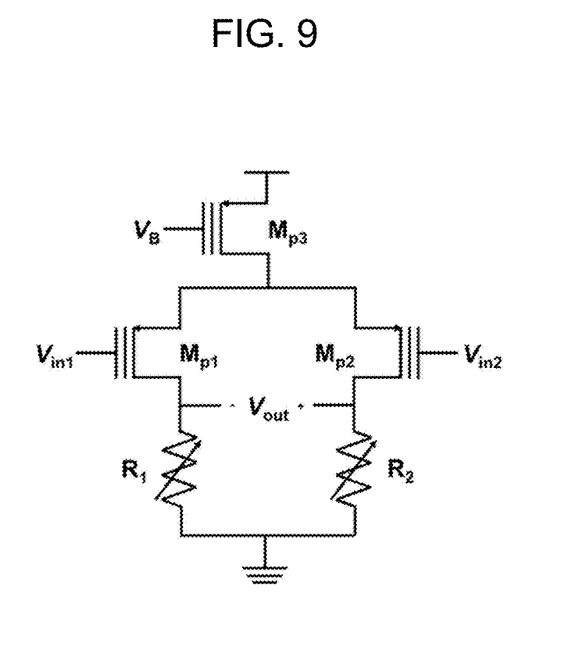
FIG. 9 is a circuit diagram of the first embodiment in the complementary sensors-integrated differential interface circuit according to Example 2 of the present invention.

FIG. 9 is a circuit diagram of the first embodiment in the complementary sensors-integrated differential interface circuit according to Example 2 of the present invention. Referring to FIG. 9, in the complementary sensors-integrated differential interface circuit according to the present embodiment, the first and second circuit units are connected in series with the first sensors ($M_{p1}$ and $M_{p2}$) and the second sensors (R1 and R2), and the first circuit unit and the second circuit unit are arranged in parallel with each other. The first sensors ($M_{p1}$ and $M_{p2}$) of the first and second circuit units are composed of pFET-type sensors, and the second sensors (R1 and R2) of the first and second circuit units are composed of resistor-type sensors. The first sensor ($M_{p1}$) of the first circuit unit and the second sensor (R2) of the second circuit unit have complementary sensing characteristics, or the second sensor (R1) of the first circuit unit and the first sensor ($M_{p2}$) of the second circuit unit have complementary sensing characteristics, or the first sensors ($M_{p1}$ and $M_{p2}$) of the first and second circuit units have complementary sensing characteristics, or the second sensors (R1 and R2) of the first and second circuit units have complementary sensing characteristics. At this time, the sensors having no complementary sensing characteristics do not respond to the detection target material, or when responding to the detection target material, the sensors having no complementary sensing characteristics have current changes in the same direction. The constant current power supply device ($M_{p3}$) may be configured as a general PMOS device and used as a current source by constantly applying the input voltage VB.

Figure 10:
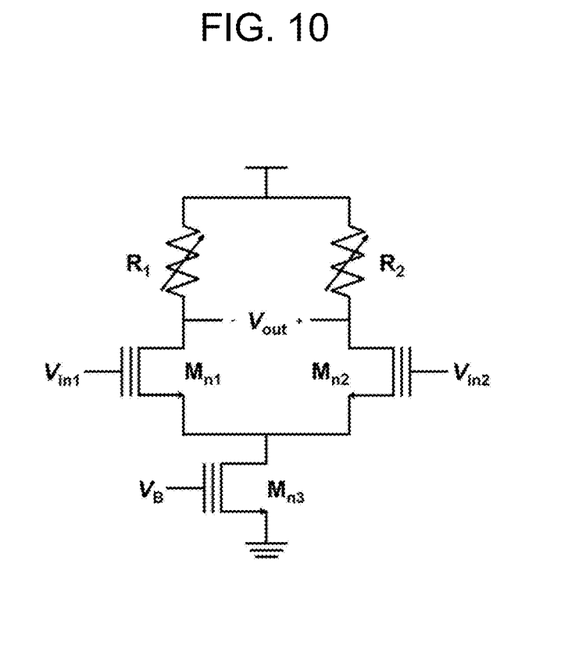
FIG. 10 is a circuit diagram of the second embodiment in the complementary sensors-integrated differential interface circuit according to Example 2 of the present invention.

FIG. 10 is a circuit diagram of the second embodiment in the complementary sensors-integrated differential interface circuit according to Example 2 of the present invention. Referring to FIG. 10, in the complementary sensors-integrated differential interface circuit according to the present embodiment, the first sensors ($M_{n1}$ and $M_{n2}$) and the second sensors (R1 and R2) of the first and second circuit units are connected in series, and the first circuit unit and the second circuit unit are arranged in parallel with each other. The first sensors ($M_{n1}$ and $M_{n2}$) of the first and second circuit units are configured as nFET-type sensors, and the second sensors (R1 and R2) of the first and second circuit units are configured as resistor-type sensors. The first sensor ($M_{n1}$) of the first circuit unit and the second sensor (R2) of the second circuit unit have complementary sensing characteristics, or the second sensor (R1) of the first circuit unit and the first sensor ($M_{n2}$) of the second circuit unit have complementary sensing characteristics to each other, or the first sensors ($M_{n1}$ and $M_{n2}$) of the first and second circuit units have complementary sensing characteristics to each other, or the second sensors (R1 and R2) of the first and second circuit unit have complementary sensing characteristics to each other. At this time, the sensors having no complementary sensing characteristics do not respond to the detection target material, or when responding to the detection target material, the sensors having no complementary sensing characteristics have current changes in the same direction. The constant current power supply device ($M_{n3}$) may be configured as a general NMOS device and used as a current source by constantly applying the input voltage $V_B$.

Figure 11:
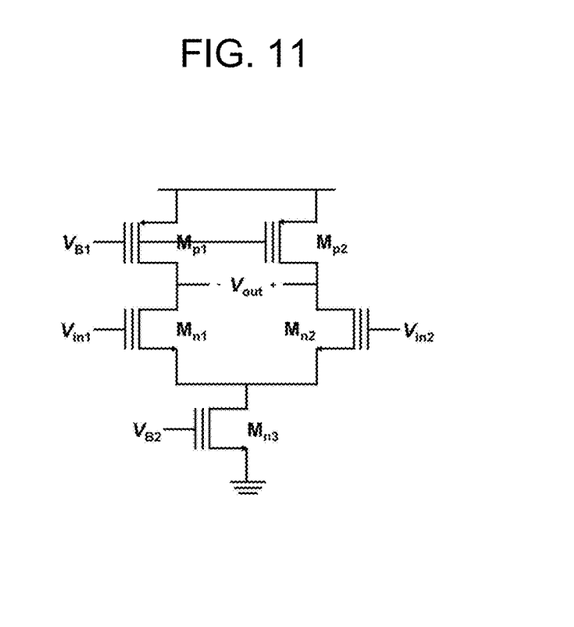
FIG. 11 is a circuit diagram of a third embodiment in a complementary sensors-integrated differential interface circuit according to Example 2 of the present invention.

FIG. 11 is a circuit diagram of a third embodiment in a complementary sensors-integrated differential interface circuit according to Example 2 of the present invention. Referring to FIG. 11, in the complementary sensors-integrated differential interface circuit according to the present embodiment, the first sensors ($M_{n1}$ and $M_{n2}$) and the second sensors ($M_{p1}$ and $M_{p2}$) of the first and second circuit units are connected in series, and the first circuit unit and the second circuit unit are arranged in parallel with each other. The first sensors ($M_{n1}$, $M_{n2}$) of the first and second circuit units are configured as nFET-type sensors, and the second sensors ($M_{p1}$, $M_{p2}$) of the first and second circuit units are configured as pFET-type sensors. The first sensor ($M_{n1}$) of the first circuit unit and the second sensor ($M_{p2}$) of the second circuit unit have complementary sensing characteristics, or the second sensor ($M_{p1}$) of the first circuit unit and the first sensor ($M_{n2}$) the second circuit unit have complementary sensing characteristics to each other, or the first sensors ($M_{n1}$ and $M_{n2}$) of the first and second circuit units have complementary sensing characteristics, or the second sensors ($M_{p1}$ and $M_{p2}$) of the first and second circuit units have complementary sensing characteristics to each other. At this time, the sensors having no complementary sensing characteristics do not respond to the detection target material, or when responding to the detection target material, the sensors having no complementary sensing characteristics have current changes in the same direction. The constant current power supply device ($M_{n3}$) may be configured as a general NMOS device and used as a current source by constantly applying the input voltage $V_{B2}$.

Figure 12:
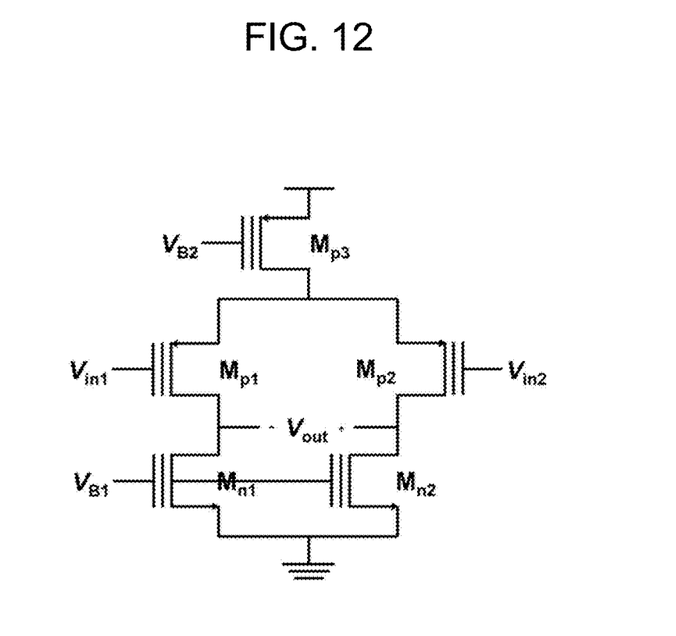
FIG. 12 is a circuit diagram of a fourth embodiment in a complementary sensors-integrated differential interface circuit according to Example 2 of the present invention.

FIG. 12 is a circuit diagram of a fourth embodiment in a complementary sensors-integrated differential interface circuit according to Example 2 of the present invention. Referring to FIG. 12, in the complementary sensors-integrated differential interface circuit according to the present embodiment, the first sensor ($M_{p1}$, $M_{p2}$) and the second sensor ($M_{n1}$, $M_{n2}$) of the first and second circuit units are connected in series, and the first circuit unit and the second circuit unit are arranged in parallel with each other. The first sensors ($M_{p1}$ and $M_{p2}$) of the first and second circuit units are configured as a pFET-type sensor, and the second sensors ($M_{n1}$ and $M_{n2}$) of the first and second circuit units are configured as an nFET-type sensor. The first sensor ($M_{p1}$) of the first circuit unit and the second sensor ($M_{n2}$) of the second circuit unit have complementary sensing characteristics to each other, or the second sensor ($M_{n1}$) of the first circuit unit and the first sensor ($M_{p2}$) of the second circuit unit have complementary sensing characteristics to each other, or the first sensors ($M_{p1}$, $M_{p2}$) of the first and second circuit units may have complementary sensing characteristics to each other, or the second sensors ($M_{n1}$, $M_{n2}$) of the first and second circuit units may have complementary sensing characteristics to each other. At this time, the sensors having no complementary sensing characteristics do not respond to the detection target material, or when responding to the detection target material, the sensors having no complementary sensing characteristics have current changes in the same direction. The constant current power supply device ($M_{p3}$) may be configured as a general PMOS device and used as a current source by constantly applying the input voltage $V_{B2}$.

Example 3

Hereinafter, a configuration and operation of a complementary sensors-integrated differential interface circuit using a complementary sensors-integrated interface circuit according to Example 3 of the present invention will be described in detail.

A complementary sensors-integrated differential interface circuit according to Example 3 of the present invention comprises first and second circuit units arranged in parallel with each other, and a constant current supply element connected in series to one end of the first and second circuit units. In the complementary sensors-integrated differential interface circuit according to Example 3 of the present invention, the first and second circuit units comprises first and second sensors connected in series with each other, respectively, and the constant current supply element provides constant current power to the first and second circuit units. In the first and second circuits, the first sensors are composed of a FET-type sensor and the second sensors are composed of an FET-type sensor, wherein the second sensors in the first and second circuits are connected to form a current mirror circuit.

A first output is provided between the first and second sensors of the first circuit unit and a second output is provided between the first and second sensors of the second circuit unit. The first and second sensors of the first and second circuit units are configured so that signals of the first and second outputs are complementary to each other. The constant current power supply element ($M_{p3}$) is used as a current source to uniformly apply a common current to the first and second circuit units.

Figure 13:
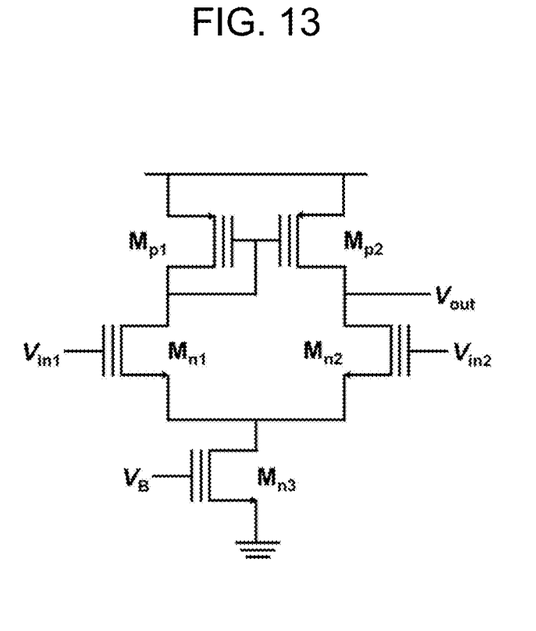
FIG. 13 is a circuit diagram of the first embodiment in the complementary sensors-integrated differential interface circuit according to Example 3 of the present invention.

FIG. 13 is a circuit diagram of the first embodiment in the complementary sensors-integrated differential interface circuit according to Example 3 of the present invention. Referring to FIG. 13, in the complementary sensors-integrated differential interface circuit according to the present embodiment, the first and second circuit units comprise a first sensor ($M_{n1}$, $M_{n2}$) and a second sensor ($M_{p1}$, $M_{p2}$) which are connected in series to each other, and the first circuit unit and the second circuit unit are arranged in parallel with each other. The first sensors ($M_{n1}$, $M_{n2}$) of the first and second circuit units are configured as nFET-type sensors, and the second sensors ($M_{p1}$, $M_{p2}$) of the first and second circuit units are configured as pFET-type sensors, and the second sensors are connected to constitute a current mirror circuit. The first sensor (Mn) of the first circuit unit and the second sensor ($M_{p2}$) of the second circuit unit have complementary sensing characteristics, or the second sensor ($M_{p1}$) of the first circuit unit and the first sensor ($M_{p2}$) of the second circuit unit have complementary sensing characteristics to each other, or the first sensors ($M_{n1}$, $M_{n2}$) of the first and second circuit units have complementary sensing characteristics to each other, or the second sensors ($M_{p1}$, $M_{p2}$) of the first and second circuit units have complementary sensing characteristics to each other. At this time, the sensors that do not have complementary sensing characteristics do not respond to the detection target material, or when responding to the detection target material, the sensors having no complementary sensing characteristics have current changes in the same direction. The constant current power supply device ($M_{n3}$) may be configured as a general NMOS device and used as a current source by constantly applying the input voltage $V_{B2}$.

Figure 14:
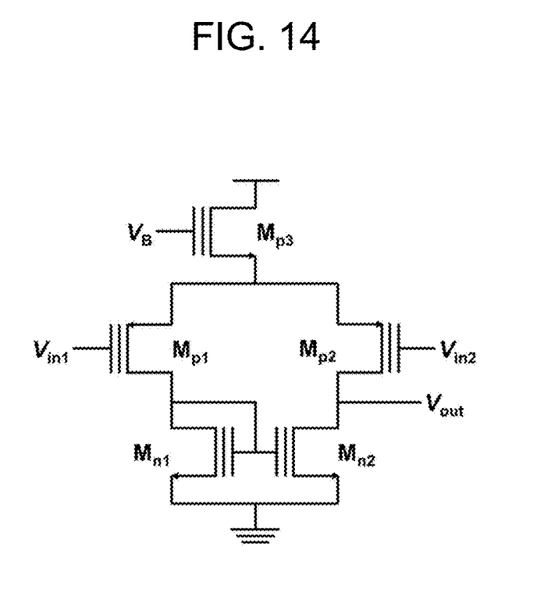
FIG. 14 is a circuit diagram of a second embodiment in a complementary sensors-integrated differential interface circuit according to Example 3 of the present invention.

FIG. 14 is a circuit diagram of a second embodiment in a complementary sensors-integrated differential interface circuit according to Example 3 of the present invention. Referring to FIG. 14, in the complementary sensors-integrated differential interface circuit according to the present embodiment, the first and second circuit units comprise a first sensor ($M_{p1}$, $M_{p2}$) and a second sensor ($M_{s1}$, $M_{s2}$) which are connected in series, and the first circuit unit and the second circuit unit are arranged in parallel with each other. The first sensors ($M_{p1}$, $M_{p2}$) of the first and second circuit units are configured as pFET-type sensors, and the second sensors ($M_{n1}$, $M_{n2}$) of the first and second circuit units are configured as nFET-type sensors, and the second sensors are connected to constitute a current mirror circuit. The first sensor ($M_{p1}$) of the first circuit unit and the second sensor ($M_{n2}$) of the second circuit unit have complementary sensing characteristics to each other, or the second sensor ($M_{n1}$) of the first circuit unit and the first sensor ($M_{p2}$) of the second circuit unit may have complementary sensing characteristics to each other, or the first sensors ($M_{p1}$, $M_{p2}$) of the first and second circuit units may have complementary sensing characteristics to each other, or the second sensors ($M_{n1}$, $M_{n2}$) of the first and second circuit units may have complementary sensing characteristics to each other. At this time, the sensors that do not have complementary sensing characteristics do not respond to the detection target material, or when responding to the detection target material, the sensors having no complementary sensing characteristics have current changes in the same direction. The constant current power supply device ($M_{p3}$) may be configured as a general PMOS device and used as a current source by constantly applying the input voltage $V_{B2}$.

The differential interface circuit according to Examples 2 and 3 described above comprises a first output provided between the first and second sensors of the first circuit unit and a second output provided between the first and second sensors of the second circuit unit. It is preferable to obtain a difference value of the current or voltage signals of the first and second outputs and provide the difference value as an output signal. In addition, the output signal of the differential interface circuit may be used in connection with a neuron circuit having a function of converting it into a pulse train or a pulse width.

Hereinafter, various structures of the FET-type sensor used in the present invention will be described with reference to FIGS. 15 to 18.

Figure 15:
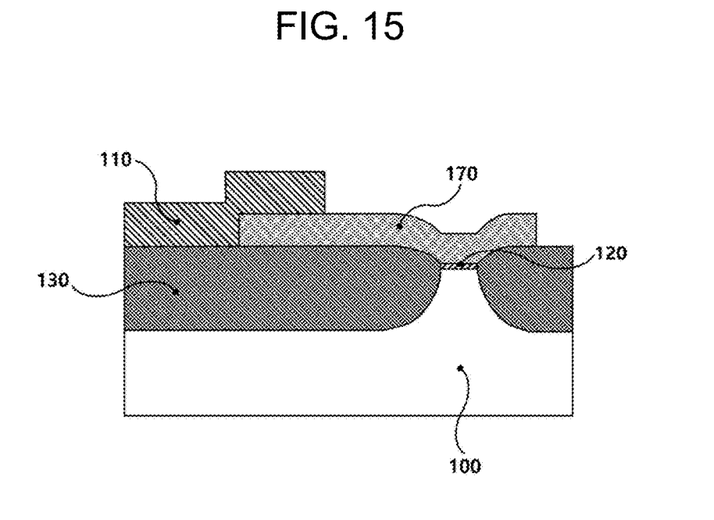
FIGS. 15, 16, 17 and 18 are cross-sectional views illustrating examples of FET-type sensors used in the complementary sensors-integrated interface circuit according to the present invention.

FIG. 15 is a cross-sectional view illustrating an example of an FET-type sensor used in a complementary sensors-integrated interface circuit according to the present invention. Referring to FIG. 15, the FET sensor comprises: a FET structure comprising at least a source (not shown), a drain (not shown), a gate insulating film (120), an isolation insulating film (130) and a control gate electrode (110) provided on a substrate (100); and a sensing material layer (170) formed on the gate insulating film of the FET structure, and operates as a sensor. The FET structure may optionally comprise body or substrate terminals. The sensing material layer (170) is provided on the gate insulating film (120), and a portion of the side and/or upper region of the sensing material layer is configured to be connected to the control gate electrode (110), thereby operating as a control gate electrode.

Figure 16:
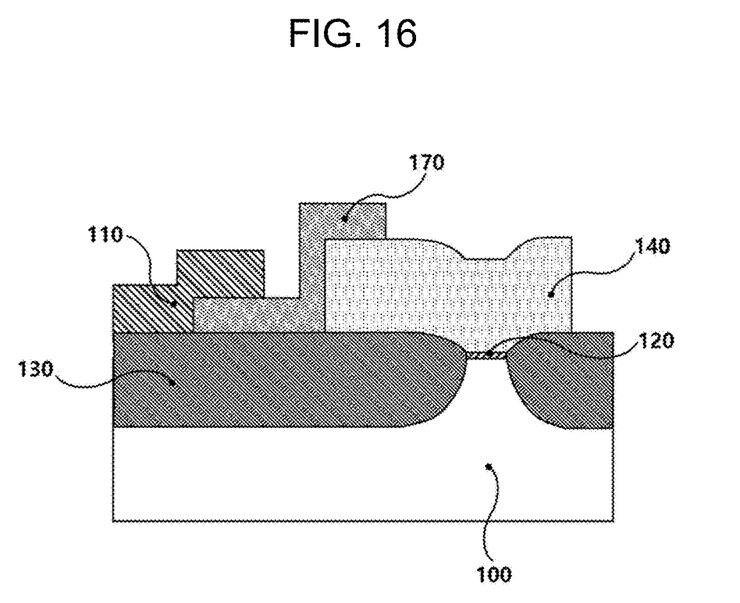

FIG. 16 is a cross-sectional view showing another example of the FET-type sensor used in the complementary sensors-integrated interface circuit according to the present invention. Referring to FIG. 16, the FET-type sensor comprises: a FET structure comprising at least a source (not shown), a drain (not shown), a gate insulating film (120), an isolation insulating film (130), a control gate electrode (110) and floating gate electrode (140) provided on a substrate (100); and a sensing material layer (170) formed in the FET structure, and operates as a sensor. The FET structure may optionally include body or substrate terminals. The sensing material layer (170) is disposed between the control gate electrode (110) and the floating gate electrode (140) to connect the control gate electrode and the floating gate electrode. The floating gate electrode (140) is provided on the gate insulating film (120), and one side and/or part of the upper region of the floating gate is connected to the sensing material layer (170), and the other side of the sensing material layer is connected to the control gate electrode.

Figure 17:
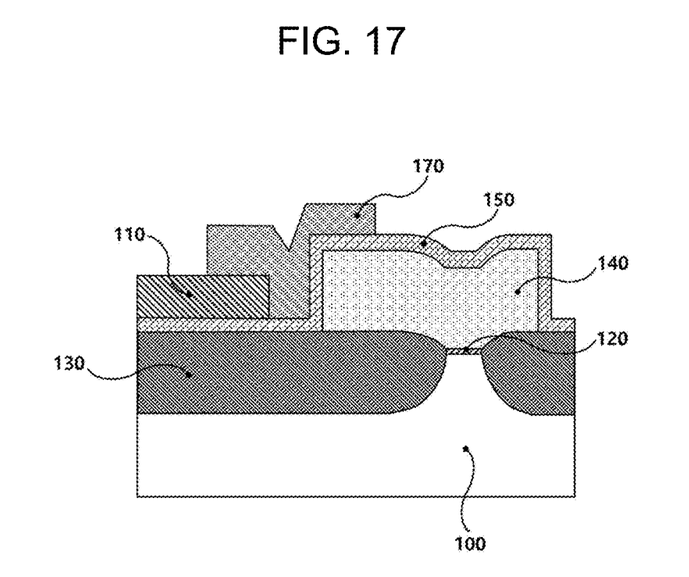

FIG. 17 is a cross-sectional view showing another example of the FET-type sensor used in the complementary sensors-integrated interface circuit according to the present invention. Referring to FIG. 17, the FET-type sensor comprises: a FET structure comprising at least a source (not shown), a drain (not shown), a gate insulating film (120), an isolation insulating film (130), a control gate electrode (110), floating gate electrode (140) and the protective insulating film (150) provided on a substrate 100; and a sensing material layer (170) formed in the FET structure, and operates as a sensor. The FET structure may optionally include body or substrate terminals. A protective insulating film (150) is formed on the surface of the floating gate electrode and the surface of the isolation insulating film (130), and a protective insulating film is interposed between the isolation insulating film and the control gate electrode. The sensing material layer (170) is disposed between the control gate electrode (110) and the floating gate electrode (140), and protective insulating films are disposed between the sensing material layer and the isolation insulating film and between the sensing material layer and the floating gate electrode. By being so interposed, the sensing material layer has a structure electrically isolated from the floating gate.

Figure 18:
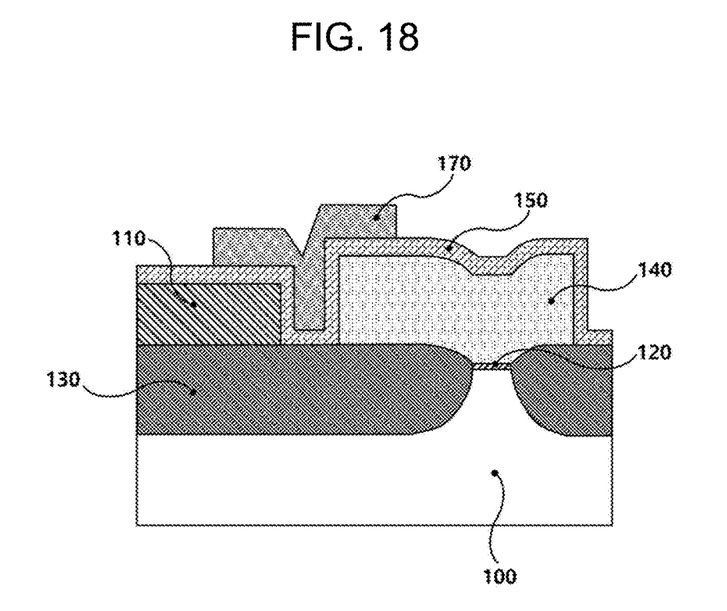

FIG. 18 is a cross-sectional view showing another example of the FET-type sensor used in the complementary sensors-integrated interface circuit according to the present invention. Referring to FIG. 18, the FET-type sensor comprises: a FET structure comprising at least a source (not shown), a drain (not shown), a gate insulating film (120), an isolation insulating film (130), a control gate electrode (110), floating gate electrode (140) and the protective insulating film (150) provided on a substrate (100); and a sensing material layer (170) formed in the FET structure, and operates as a sensor. The FET structure may optionally comprise body or substrate terminals. The floating gate electrode and the control gate electrode are formed to be separated from each other on the gate insulating film and the isolation insulating film, and a protective insulating film (150) is formed on the surface of the floating gate electrode and the control gate electrode, and the surface of the isolation insulating film (130) in which the floating gate electrode and the control gate electrode are not formed. The sensing material layer (170) is disposed between the control gate electrode (110) and the floating gate electrode (140) on which a protective insulating film is applied, and a protective insulating film is also interposed between the sensing material layer and the isolation insulating film. By being so interposed, the sensing material layer has a structure electrically isolated from the floating gate electrode and the control gate electrode.

In the above-described FET sensors shown in FIGS. 16, 17 and 18, preferably the control gate electrode and the floating gate electrode are implemented in an interdigitated structure to increase the coupling ratio.

The above-described FET-type sensors may be implemented as p-type or n-type, and may comprise an embedded micro-heater. The sensing material may be a film made of a material such as metal, metal-oxide, semiconductor, etc., or a two-dimensional material (eg, graphene, graphene oxide, $MOS_2$ etc.) having a nano-sized structure such as nano dots, nano tubes, and nano wire, etc.

In the above, the present invention has been mainly described with respect to its preferred embodiment, but this is only an example and does not limit the present invention. Those of ordinary skill in the art to which the present invention pertains will appreciate that various modifications and applications not exemplified above are possible without departing from the essential characteristics of the present invention. And, the differences related to such modifications and applications should be construed as being included in the scope of the present invention defined in the appended claims.

What is claimed is:

1. A complementary sensors-integrated interface circuit, the interface circuit comprising:
    a first sensor having a first characteristic for sensing a detection target material; and
    a second sensor having a second characteristic for sensing the detection target material, which the second characteristic is complementary to the first characteristic,
    wherein the first sensor is composed of a first FET-type sensor, the second sensor is composed of a second FET-type sensor or a resistor-type sensor, and the first sensor and the second sensor are connected in series,
    wherein the FET-type sensor comprises:
    a source, a drain, a gate insulating film and an isolation insulating film formed on a substrate;
    a floating gate electrode formed on a portion of a surface of the gate insulating film;
    a control gate electrode formed on a portion of a surface of the isolation insulating film; and
    a sensing material layer formed by coating a sensing material over a portion of a surface of the isolation insulating film, a portion of the control gate electrode, and a portion of the floating gate electrode, and
    wherein the FET-type sensor is composed of a memory-type FET, so that the threshold voltage (Vth) of the gate electrode can be adjusted.

2. The complementary sensors-integrated interface circuit according to claim 1, wherein the first sensor is composed of the first FET-type sensor with a p-type or n-type channel, and the second sensor is composed of the resistor-type sensor or the second FET-type sensor with a channel of a type opposite to that of the first sensor.

3. The complementary sensors-integrated interface circuit according to claim 1, wherein the sensing materials of the first and second sensors are of the same type.

4. The complementary sensors-integrated interface circuit according to claim 1, wherein the first FET-type sensor includes a pFET-type sensor, and the second FET-type sensor includes an nFET-type sensor, respectively, and
    the first and second sensors share a sensing material layer with each other, and
    the first and second sensors share input power applied to the control gate electrodes of the first and second sensors.

5. The complementary sensors-integrated interface circuit according to claim 1, wherein the first FET-type sensor includes a pFET-type sensor, and the second FET-type sensor includes an nFET-type sensors, and
- the first sensor and the second sensor have separate sensing material layers, and
- the first sensor and the second sensor share input power applied to the control gate electrodes with each other.

6. A complementary sensors-integrated interface circuit, the interface circuit comprising:
- a first sensor having a first characteristic for sensing a detection target material; and
- a second sensor having a second characteristic for sensing the detection target material, which the second characteristic is complementary to the first characteristic,
- wherein the first sensor is composed of an FET-type sensor, the second sensor is composed of an FET-type sensor or a resistor-type sensor, and the first sensor and the second sensor are connected in series,
- wherein the FET-type sensor comprises:
- a source, a drain, a gate insulating film and an isolation insulating film formed on a substrate;
- a sensing material formed on a portion of a surface of the gate insulating film; and
- a control gate electrode formed on a portion of the isolation insulating film and a portion of the surface of the sensing material layer, and
- wherein the sensing material layer is connected to the control gate electrode.

7. The complementary sensors-integrated interface circuit according to claim 1, wherein the FET-type sensor is characterized in that
- a protective insulating film is interposed between the floating gate electrode and the sensing material layer or between the floating gate and the control gate electrode and the sensing material layer, so that the sensing material layer is either electrically isolated from the floating gate electrode or electrically isolated from the floating gate electrode and the control gate electrode.

8. A complementary sensors-integrated differential interface circuit comprising: first and second circuit units connected in parallel with each other; and a constant current supply element connected in series to one end of the first and second circuit units, the first and second circuit units sharing the current supply element,
- wherein the first and second circuit units both include first and second sensors having a characteristic for sensing a detection target material, wherein the first sensor and the second sensor are connected in series,
- the constant current supply element provides the constant current power to the first and second circuit units,
- the first sensors of the first and second circuit units are composed of an FET-type sensor and the second sensors of the first and second circuit units are composed of a FET-type sensor or a resistor-type sensor, and
- a first output is provided between the first and second sensors connected in series in the first circuit unit, and a second output is provided between the first and second sensors connected in series in the second circuit unit, and the first and second sensors of the first and second circuit units are configured so that signals of the first and second outputs are complementary to each other.

9. The complementary sensors-integrated differential interface circuit according to claim 8, wherein the second sensors of the first and second circuit units are connected to constitute a current mirror circuit.

10. The complementary sensors-integrated differential interface circuit according to claim 8, wherein the first sensor of the first circuit unit and the second sensor of the second circuit unit operate in a complementary manner, or
- the second sensor of the first circuit unit and the first sensor of the second circuit unit operate in a complementary manner.

11. The complementary sensors-integrated differential interface circuit according to claim 8, wherein the first sensors of the first and second circuit units are composed of the same type of sensor using the same sensing material,
- the second sensors of the first and second circuit units are composed of sensors operating in a complementary manner to each other.

12. The complementary sensors-integrated differential interface circuit according to claim 8, wherein the second sensors of the first and second circuit units are composed of the same type of sensor using the same sensing material,
- the first sensors of the first and second circuit units are composed of sensors operating in a complementary manner to each other.

13. The complementary sensors-integrated differential interface circuit according to claim 8, wherein all sensors provided in the first and second circuit units are composed of the same sensor or the same type of sensor using the same sensing material,
- and the first and second sensors having complementary sensing characteristics to each other in the first and second circuit units are configured so that the first and second outputs are complementary to each other.

14. The complementary sensors-integrated differential interface circuit according to claim 8, wherein the first and second sensors having complementary characteristic for sensing the detection target material to each other in the first and second circuit units include opposite types of sensing materials so that the first and second outputs are complementary to each other.

15. The complementary sensors-integrated differential interface circuit according to claim 8, wherein the FET-type sensor comprises:
- a source, a drain, a gate insulating film and an isolation insulating film formed on a substrate;
- a sensing material formed on a portion of a surface of the gate insulating film; and
- a control gate electrode formed on a portion of the isolation insulating film and a portion of the surface of the sensing material layer, and
- wherein the sensing material layer is connected to the control gate electrode.

16. The complementary sensors-integrated differential interface circuit according to claim 8, wherein the FET-type sensor comprises:
- a source, a drain, a gate insulating film and an isolation insulating film formed on a substrate;
- a floating gate electrode formed on a portion of a surface of the gate insulating film;
- a control gate electrode formed on a portion of a surface of the isolation insulating film; and
- a sensing material layer formed by coating a sensing material over a portion of the surface of the isolation insulating film, a portion of the control gate electrode, and a portion of the floating gate electrode, and
- wherein the FET-type sensor is composed of a memory-type FET, so that the threshold voltage (Vth) of the gate electrode can be adjusted.

17. The complementary sensors-integrated differential interface circuit according to claim 16, wherein the differential interface circuit further comprises:
a protective insulating film which is interposed between the floating gate electrode and the sensing material layer or between the floating gate and the control gate electrodes and the sensing material layer, so that the sensing material layer is either electrically isolated from the floating gate electrode or electrically isolated from the floating gate electrode and the control gate electrode.

* * * * *